United States Patent [19]

Hazen

[11] Patent Number: 5,824,797

[45] Date of Patent: Oct. 20, 1998

[54] GUAR AS A DEPOSITION AND BIOEFFICACY AID

[75] Inventor: James Lyle Hazen, Plainsboro, N.J.

[73] Assignee: Rhone-Poulenc Inc., Cranbury, N.J.

[21] Appl. No.: 494,481

[22] Filed: Jun. 26, 1995

Related U.S. Application Data

[63] Continuation-in-part of Ser. No. 177,051, Jan. 3, 1994, Pat. No. 5,550,224.

[51] Int. Cl.$^6$ ............... C08B 37/00; C07H 1/00; A01N 43/04; A61K 31/715
[52] U.S. Cl. ............... 536/114; 536/123; 536/123.1; 514/54
[58] Field of Search ............... 536/114, 123, 536/123.1; 514/54

[56] References Cited

U.S. PATENT DOCUMENTS

| | | | |
|---|---|---|---|
| 3,918,935 | 11/1975 | Livingston | 55/228 |
| 4,510,081 | 4/1985 | Bronner et al. | 252/603 |
| 4,870,167 | 9/1989 | Zody et al. | 536/114 |

*Primary Examiner*—John Kight
*Assistant Examiner*—Everett White
*Attorney, Agent, or Firm*—Katherine L. Carleton

[57] ABSTRACT

Aerial spray or discharge drift is reduced, deposition improved and bioefficacy enhanced in aqueous compositions via the use of selected non-visco-elastic amounts of guar, one or more derivatives of guar or combinations thereof.

35 Claims, 2 Drawing Sheets

CHAMBER ENTRANCE

DIRECTION OF SPRAYER TRAVEL →

COLLECTION SURFACE

ANGLED LEAF SUPPORT

GUAR AS A DEPOSITION AND BIOEFFICACY AID

This application is a continuation-in-part of U.S. application Ser. No. 08/177,051, filed Jan. 3, 1994, now U.S. Pat. No. 5,550,224.

BACKGROUND OF THE INVENTION

1. Field of the Invention

This invention relates to the control of droplet-size distributions in aqueous aerial sprays or discharges and, more particularly, relates to the minimization of spray drift and the enhancement of deposition and bioefficacy.

2. Description of the Prior Art

Mist, or the fine particles end of the droplet-size spectra (typically those less than 150 microns in diameter) in industrial aqueous spray or discharge processes, such as those associated with aerial firefighting and dust control, gas scrubbers, crude oil spill treatments and various bioactive ingredient application processes, particularly those associated with agriculture, often reduce the effectiveness of these processes.

When the sprays are to be directed toward a specific target, the aerial spray or discharge delivery systems are typically mounted on airplanes, tractors, ground rigs or railcars. However, as a result of spray drift, much of the material in a spray can be rendered ineffective because of the inability of the small diameter spray particles to reach and impact upon the intended target. It is well known that spray droplet-size is a major factor affecting drift. While small droplets provide better coverage of a target, they are more susceptible to drift than larger droplets. Spray drift represents a loss of chemical from intended targets and thus implies the dangers inherent in air and water pollution. Since off-target chemicals are wasted product and with agricultural sprays, in particular, can represent a hazard to surrounding crops, water supplies and livestock, spray drift is an economical and environmental concern.

Research efforts to reduce spray drift have typically dealt with improved equipment design, e.g., nozzle design to optimize spray patterns, or application techniques such as spray pressures, heights, formulations, etc. The most promising improvements in the application technology area have been in the reduction of fine spray droplets in the droplet spectrum during atomization via the use of spray modifiers known as drift control agents. Effective drift control agents must possess a great number of characteristics for they must be able to increase the small droplet size; be insensitive to the high shear process conditions realized in the spray system pumps, nozzles, etc.; not detract from the biological effects of the spray bioactives; be compatible with other spray adjuvants, i.e., non-bioactive material added to the spray mixture to improve chemical or physical characteristics; not separate upon standing; be easy to use; be environmentally friendly; and be cost efficient.

Drift control agents are usually high molecular weight polymers which, when added to aqueous systems, tend to increase the viscosity of the system and thus prevent the water from being broken up into a fine mist when aerially sprayed or discharged.

These high molecular weight polymers tend to be unstable in that they often degrade upon aging and are very shear sensitive: both of which conditions, upon occurrence, cause a decrease in solution viscosity with a concomitant decrease in drift control activity.

Typical polymers currently utilized as drift control agents are the visco-elastic polyacrylamides, the polyethylene oxides, and the poly (vinyl pyrrolidones), with the polyacrylamides being the agriculture industry spray tank additive, drift reduction standard. However, current polyacrylamide drift control spray formulations have a very limited effective time of positive drift reduction for a number of reasons. At the outset, the synthetic polyacrylamide polymer drift control agents are usually distributed in a kerosene carrier, which limits the dispersibility and additionally presents a volatile organic component problem for the end user. The polymers themselves are essentially non-biodegradable. Furthermore, specific organic inverting surfactants must be used with these polymers to enable them to be properly hydrated and dispersed in water. Some of these polymers have also demonstrated a sensitivity to water quality. Of course, all of the above necessitates the use of plastic (or glass) containers; a decided disadvantage.

Finally, and perhaps most importantly, these high molecular weight synthetic polyacrylamide polymers are extremely sensitive to shear stresses. Shear stressing is caused by high pressure gradients which may be imposed on a liquid by flow controllers, turbine metering systems, pumps and, in general, pressure differentials exceeding about 40 psi such as is commonly associated with aerial spray nozzles and discharge systems. Unfortunately, shear stressing damages shear-sensitive visco-elastic polymers such as the polyacrylamides by a phenomenon known as physical shear degradation. This degradation of the polymer realizes a significant decrease in solution viscosity which results in a lessening of the droplet-size distribution control effects.

In summary, the polyacrylamide drift-reducing products have several major characteristics that are not conducive to ease of use or reliable efficiency: slow hydration, water quality sensitivity and, most importantly, shear sensitivity.

Another need in the industrial aqueous spray or discharge systems is for deposition aids, i.e., materials that improve the ability of actives, such as pesticides, herbicides, fungicides and the like, to deposit on targeted surfaces. Improved deposition allows for reductions in the amount of actives utilized which in turn reduces economical and environmental concern.

Additives which can enhance the bioefficacy of the actives can also be beneficial since more active potential allows for reductions in the amount of chemicals utilized. A multifunctional additive for industrial aqueous spray or discharge which can provide excellent drift control, improved deposition, and enhanced bioefficacy.

BRIEF DESCRIPTION OF THE DRAWINGS

FIG. 1 is a side view schematic diagram of a standard reflection chamber used to calculate the spray mixtures droplet reflection/retention characteristics.

FIG. 2 is a bar graph comparing the degree or percentage amount of solution reflected for water, Nalcotrol II polymer solution and a solution of the present invention.

FIG. 3 is a bar graph comparing three different drift reducing adjuvants on the killing efficacy of a commercially available herbicide on a common weed, velvetleaf.

SUMMARY OF THE INVENTION

It has now been discovered that guar and derivatives of guar can be utilized in an aqueous spray medium as excellent drift control agents with essentially none of the above-identified disadvantages associated with the polyacrylamide agents. When used in amounts such that, if used in water alone, the guar-water combinations would exhibit Newtonian liquid behavior, guar and its derivatives effectively reduce the number of droplets below about 150 microns, i.e. the droplets most responsible for drift problems; exhibit rapid dispersion and hydration in water, and are ion insensitive, i.e. not dependent on water quality.

In addition to being biodegradable, the initial guar materials are dry and, thus are not subject to separation upon storage, nor are they freeze sensitive. No volatile organic compound carriers are needed nor is there a need for surfactants to affect rapid hydration in water.

The guar compositions of this invention not only possess the highly desirable characteristics of efficient drift control agents, but also maintain these properties under prolonged high shear commercial spray conditions, i.e., the guar compositions of this invention are highly resistant to shear scission and degradation of the drift reduction effect for which these adjuvants are intended.

It has been discovered that guar and derivatives of guar can be utilized in an aqueous spray medium as excellent deposition aids. The guar and derivatives of guar significantly improve the ability of actives, such as pesticides, to deposit on targeted surfaces without a negative effect on drift control.

It has also been discovered that guar and derivatives of guar can be utilized in an aqueous spray medium for obtaining improved biological efficacy of bioactives.

DETAILED DESCRIPTION OF THE INVENTION

The essence of this invention lies in the discovery that very small amounts of guar (0.075 to less than 0.2% weight per unit volume (w/v)), one or more non-cationic derivatized guars (0.075 to 0.275% w/v), or one or more cationic guars (0.05 to 0.1% w/v), or combinations thereof, in aqueous spray or discharge compositions at final dilution (the final spray composition) can function as an extremely effective drift reduction control agent and, serendipitously, in these low concentration ranges, exhibits Newtonian behavior, i.e., is not shear sensitive, as well as function as a deposition aid and bioefficacy aid. These concentration ranges are far below that previously disclosed (typically in excess of 0.6% w/v) for the utilzation in aqueous compositions of the other art recognized characteristics of guar and its derivatives, such as their ability to act as a lubricant, a binder, a thickener or a suspension agent.

Guar gum is the refined endosperm of the legume seed of *Cyamopsis tetragonolobus* (L.) Taub., a plant which physically resembles the soy plant. The gum is a pure food vegetable colloid recognized by the agricultural, chemical and food formulation industry for many years as having excellent thickening, film-forming and stabilizing properties.

Guar is often used in foods as a thickener and a binder of free water. In salad dressings, guar raises the viscosity of the emulsion and decreases the separation rate. Because guar functions to bind free water, it is used to stabilze foods such as ice cream by inhibiting the formation of ice crystals. Guar is also utilized to stabilze certain delicate, non-food emulsions such as 1:1 mixtures of water and mineral oil.

Guar has been shown to be useful as a lubricant not only by facilitating smooth extrusions at low pressures, but the additions of small amounts of guar have resulted in the reduction of frictional pressure drops in process water lines by up to 50%, thus increasing pump life and capacities and decreasing power requirements.

Functionally, guar is a cold water swelling, nonionic polysaccharide which develops and maintains its properties over a wide pH range. The guar polysaccharide is a complex carbohydrate polymer composed of essentially a straight chain of mannose units with single-membered galactose branches; chemically classified as a polygalactomannan.

Guar solutions are simply prepared by rapidly sifting dry gum into a vigorously agitated tank of water and permitting the gum to hydrate. Higher water temperatures can shorten the hydration time so long as the heating is not so prolonged or excessive as to degrade the polymer.

At concentrations used in this invention, solutions of guar have a zero yield value, i.e., they begin to flow at the slightest shear.

The nature of guar allows almost constant viscosity for a given solution concentration over the pH range of 3–10. Above pH 11, a lower viscosity results from the decreased ability of the gum to hydrate. The optimum hydration range occurs between pH 5 and 8. This unusual compatibility of guar over the 3–10 pH range is attributed to the nonionic nature of the molecule.

Etherification and esterification reactions are made on the guar hydroxyl functionalities. The $C_6$ hydroxyl position is the most reactive position for etherification, for example, with propylene oxide, but the secondary hydroxyls are also probable sites.

Principle etherification reactions are carboxymethylation via monochloroacetic acid, hydroxyalkylation via ethylene oxide or propylene oxide, and quaternization with various quaternary amine compounds containing reactive epoxide or chloride sites. Anionic and cationic sites modify the way the guar molecule interacts with inorganic salts, hydrated cellulosic and mineral surfaces, and organic particulates.

In general, the hydroxyalkyl ethers of polygalactomannans are prepared by reacting the polygalactomannans with alkylene oxides under basic conditions. In U.S. Pat. Nos. 3,723,408 and 3,723,409, guar flour is reacted with alkylene oxides in the presence of water and sodium hydroxide. The reaction product is then neutralized with acid, washed with an alcohol-water mixture, and is then dried and ground. In U.S. Pat. No. 3,483,121, the polygalactomannans and the alkylene oxides are reacted under basic conditions with small amounts of water and larger amounts of water miscible or water immiscible organic solvents.

Specific hydroxyalkylating agents include ethylene oxide, propylene oxide-1,2; butylene oxide-1,2; hexylene oxide-1, 2; ethylene chlorohydrin; propylene chlorohydrin; and epichlorohydrin.

Hydroxypropylation increases the gum's solubility, resulting in a product which hydrates rapidly, regardless of water temperature. Hydroxyalkyl derivatives are more tolerant of the water-miscible solvents and thus can swell in and develop viscosity in aqueous solutions containing low molecular weight organic solvents such as methanol, ethanol, etc. Both hydroxyalkyl and carboxymethyl derivatives typically form clearer solutions than standard guar gum and also hydroxyalkyl derivatives resist thermal degradation better than standard guar. Hydroxypropyl guar is particularly useful as a flow modifier and friction reducing agent which does not flocculate solids.

Carboxyalkyl ethers and mixed carboxyhydroxyallyl ethers of polygalactomannans are described in U.S. Pat. Nos. 3,740,388 and 3,723,409, respectively. These derivatives are made by reacting the polygalactomannan with the derivatizing agents (halofatty acid and alkylene oxide) in a water-alcohol mixture followed by washing with water-alcohol mixtures.

Specific carboxyalkylating agents include chloroacetic acid, chloropropronic acid, and acrylic acid.

Carboxymethylation introduces an anionic function to the polymer chain and further increases the solubility of guar. Carboxymethyl hydroxypropyl guar is exceptional in its ability to suspend undissolved solids.

Other derivatives of polygalactomannans are described in such patents as U.S. Pat. No. 2,461,502 (cyanoethyl ethers), U.S. Pat. No. 4,094,795 (dialkylacrylamide ethers) and U.S. Pat. No. 3,498,912 (quaternary ammonium alkyl ethers). In the described processes, the reactions are conducted in water-organic solvent mixtures and the reaction products are washed with solvents of water solvent mixtures.

Specific quaternary ammonium alkylating agents are such agents as 2,3-epoxypropyl trimethylammonium chloride, 3-chloro-2-hydroxypropyl trimethylammonium chloride and the like.

Other agents that can react with the hydroxyl groups of the polygalactomannans to form ether groups are, for example, alkylating agents which include methyl chloride, methyl bromide, ethyl chloride, ethyl iodide and isopropyl chloride; aminoalkylating agents; such as aminoethyl chloride, aminopropyl bromide, and N,N-dimethylaminopropyl chloride; ethylenically unsaturated group containing agents which react through Michael addition with hydroxyl groups such as acrylamide, methacrylamide, acrylonitrile, methacrylonitrile, acrylic acid, sodium acrylate and, in fact, any of the polymerizable monomers which contain one ethylenically unsaturated polymerizable group.

The term "derivatized guar" is meant to include any of the above described derivatized guar products.

Guar, derived from a nitrogen-fixing, renewable resource, is a versatile, environmentally friendly, highly biodegradable polymer. Derivatized guars are slightly less sensitive to biological degradation, as the molecules are less suitable as food for common organisms.

The aqueous spray compositions of this invention are those containing water as the major component, i.e., greater than 50% by weight. Industrial aqueous spray compositions will, of course, contain in addition to the guar and guar derivatives of this invention, at least one chemically reactive compound (an actice). In the agricultural art, the compound is usually a bioactive pesticide. Other bioactives include growth regulators, herbicides, fungicides and the like. Other adjuvants in a guar aqueous spray composition may include minor amounts of, for example, buffering agents, defoaming agents, surfactants, wetting agents, sticking agents, tank cleaners, and other additives well known in the art.

The term "aerial spraying or discharging" means the spray or discharge process that occurs with commercial delivery systems typically mounted on airplanes, tractors, ground rigs or railcars and is not meant to include processes wherein drift is not a problem, e.g. totally enclosed systems such as spray dryers or low pressure, low shear, hand-held consumer application processes such as those associated with watering cans.

To provide effective spray drift reduction control of aqueous compositions, the effects realized by the drift control agent must be predictable and constant, i.e., the effects should not change with time or shear conditions.

Investigations of droplet spectra in air from industrial spray nozzles, especially those produced by most agricultural nozzles, have increasingly relied on laser-based devices. The spray cloud studies of this invention utilized the laser-based PDPA-100 system from Aerometrics Inc. for assessing the droplet spectra temporally. The drop-size ranges of the PDPA (about a 35 fold range) were sufficient to cover the droplet spectra produced by the equipment and processing conditions used in our study, i.e., flat fan agricultural-type nozzles atomizing conventional agricultive formulations at normal pressures. The methodology conformed to GLP standards.

Generally, compounds were added to thirty (30) liters of water at 26° C., then recycled and atomized through a Teejet XR8003VS nozzle at forty (40) psi. The first atomization measurement was taken after about two minutes of recycling, subsequent measurements occurred at 3–4 minute intervals. A single X-axis traverse of the spray cloud was taken. Time to traverse was adjusted so that at least 10,000 drops were counted; in most cases, it was closer to 20,000.

The spray spectra droplet diameters measured were from a maximum size of about 800 microns to a minimum size of about 20 microns.

It is generally agreed that the spray droplet sizes most susceptible to drift are those below about 150 microns. The preferred range of droplet size diameters for commercial aerial sprays lies from about 200 microns to about 500 microns.

A number of formulations were atomized both with and without drift control adjuvants. Water was used as a standard in our tests because many formulations, particularly those containing wettable powders, atomize similarly to water if adjuvants are not present.

Droplet frequency distribution data from nozzles, specifically agricultural nozzles, tend to take the form of an approximate skewed log-normal distribution. The two most commonly used terms to describe such distributions are the Volume Median Diameter ($D_{v0.5}$) and the Number Median Diameter (NMD), the diameters below which 50% of the total volume and number of drops of liquid sprayed is in drops of smaller diameter, respectively.

V% and N% depicts the proportion of the volume of the spray cloud/number of drops contained within (above/below) given size ranges.

10% Point (10% Pnt) and 90% Point (90% Pnt) means that drop size below which 10% (or 90% respectively) of the volume of the measured drops lie.

Drift of aerial sprays, especially those sprays associated with the agricultural industry, are major contributors to the wasteful nature of commercial spray applications and impacts upon public health concerns and environmental costs. Since the application equipment associated with such sprays is unlikely to significantly improve near term, the spray modifiers of the instant invention are especially valuable in obviating the above concerns and can potentially extend the life span of both new and existing active chemicals, especially the bioactive pesticides of the crop protection industry.

With the high cost of pesticides and consumers' growing concerns about hazards, accurate application has never been more important. A material which improves the ability of aqueous sprays to deposit on targeted surfaces can potentially reduce the amount of bioactives utilized while increasing or improving their effectiveness and mitigating adverse environmental effects of the application. Bioactives include pesticides (including insecticides, herbicides, rodenticides, miticides, fungicides and the like), plant growth regulators and the like. If more of the spray is depositing on the targeted surfaces, less bioactive can be utilized. This presents an economic and environmental advantage. It has been discovered that the guar and derivatives of guar are excellent deposition aids when utilized in accordance with the present invention. They can improve the ability of aqueous sprays to deposit on targeted surfaces by as much as about 30%.

A method for improving the deposition during aerial spray or discharge of an aqueous composition containing a major amount of water, greater than about 50% and preferably greater than about 75%, comprises admixing prior to application a deposition aid comprising guar and/or derivatives of guar in a sufficient amount such that if used in water alone the guar and/or derivatives of guar in water exhibit Newtonian liquid behavior prior to spraying. The deposition aids can be nonderivatized guar, one or more non-cationic derivatized guars, or one or more cationic derivatized guars, or combinations thereof.

Preferably, the nonderivatized guar is present in the aqueous spray or discharge compositions at final dilution (the final spray composition) from 0.035% to 0.20%, more preferably from 0.075% to 0.18%, weight per unit volume. Preferably, the non-cationic derivatized guars are present at final dilution (the final spray composition) from 0.035% to 0.275%, more preferably from 0.035% to 0.11% and most preferably from 0.04% to 0.11%, weight per unit volume. Preferably, the cationic derivatized guars are present at final dilution (the final spray composition) from 0.025% to 0.1%, more preferably from 0.035% to 0.05%, weight per unit volume.

Preferably, the guar and/or derivatives of guar are the sole deposition aids present in the composition and most preferably the guar and derivatives of guar are the sole deposition aid and sole drift control agent in the aqueous compositions.

Bioefflicacy (biological efficacy) functionality is independent of an adjuvant's ability to aid drift control or deposition. One skilled in the art would not expect an adjuvant that improved drift control or deposition of having an excellent ability to improve the bioefficacy of bioactives. An adjuvant which could improve drift control, deposition and the bioefficacy of bioactives would present significant economic and environmental advantages. It has been discovered that the guar and derivatives of guar of the present invention provide an excellent method for improving the bioefficacy of bioactives. They are especially effective when utilized in combination with herbicides and insecticides. This is true even on hard to wet surfaces such as velvetleaf (*Abutilon theophrastii*) and cole crops (*Brassica* species).

A method for improving/enhancing the bioefficacy of bioactives during aerial spray or discharge of an aqueous composition comprising water, generally greater than about 50%, and preferably greater than about 75%, and a biologically effective amount of a bioactive, comprises admixing prior to application to the targeted surface, a bioefficacy aid comprising guar and/or derivatives of guar in a sufficient amount such that if used in water alone the guar and/or derivatives of guar and water exhibit Newtonian liquid behavior. The bioefficacy aids can be nonderivatized guar, one or more non-cationic derivatized guars or one or more cationic derivatized guars, or combinations thereof. Preferably, the nonderivatized guar is present in the aqueous spray or discharge compositions at final dilution (the final spray composition) from 0.035% to 0.20%, more preferably from 0.075% to 0.18%, weight per unit volume. Preferably, the non-cationic derivatized guars are present at final dilution (the final spray composition) from 0.035% to 0.275%, more preferably from 0.035% to 0.11% and most preferably from 0.04% to 0.11%, weight per unit volume. Preferably, the cationic derivatized guars are present at final dilution (the final spray composition) from 0.025% to 0.1%, more preferably from 0.035% to 0.05%, weight per unit volume. The guar and/or derivatives of guar can be the sole bioefficacy aid or utilized with other bioefficacy aids. Preferably they are utilized as the sole deposition aid and drift control agents in the aqueous compositions.

Bioactives such as pesticides and particularly herbicides are more efficacious in the presence of the biodegradable guar and derivatives of guar. It is hypothesized that the properties of guar and/or derivatized guar play a role in the uptake and translocation of the bioactives in plant systems by their action on the surface.

The following examples are given to illustrate the invention and should not be construed as limiting its scope. Unless otherwise indicated, all parts and percentages are by weight of final product volume.

EXAMPLE I

The following are the results realized in a hydration rate/mixing series of studies comparing an industry standard polyacrylamide drift control agent with two derivatized guars, i.e., a hydroxy propyl guar and a carboxymethyl hydroxy propyl guar.

The polymers were added to a forty five (45) liter spray tank containing thirty (30) liters of tap water. The guar derivative powders were added by tapping them onto the surface of the water where the recycling liquid was returned from the pump. The polyacrylamide was added from a twenty (20) milliliter syringe into the same area. Both were stirred briefly by hand with a stirring rod.

The mixtures were atomized as soon as mixing was complete (after approximately two minutes), i.e., when most solid material had disappeared. The initiation of the atomization was considered time zero. The liquid was recycled with no pressure restriction, i.e., the material recycled freely through the pump, except when spraying, to simulate field tank mixng.

Droplet spectra data were measured for a single ninety (90) second traverse of the long axis of the spray cloud at each hydration/mixing interval. The intervals used were 5, 30, and 60 minutes. All guar mixtures were added to give 0.1% weight per unit volume and the polyacrylamide added to give 0.0625% volume per unit volume to achieve comparable viscosities. The liquid temperature was 25° C.±2° C. Data in all the Examples are reported in microns (mm).

TABLE I

| HYDRATION/MIXING STUDY | | | | |
|---|---|---|---|---|
| NALCOTROL II (i) HYDRATION TIME (MIN.) | 10% Pnt | NMD | % V < 100 $\mu m^{(iv)}$ | % V < 150 $\mu m$ |
| 5 | 211.3 | 53.7 | 1.85 | 4.12 |
| 30 | 202.4 | 48.5 | 2.00 | 5.05 |
| 60 | 175.4 | 47.9 | 2.75 | 7.03 |

TABLE I-continued

HYDRATION/MIXING STUDY

| JAGUAR 8000 (ii) HYDRATION TIME (MIN.) | 10% Pnt | NMD | % V < 100 μm | % V < 150 μm |
|---|---|---|---|---|
| 5 | 203.3 | 43.8 | 2.36 | 5.43 |
| 30 | 214.3 | 44.0 | 1.89 | 4.56 |
| 60 | 194.4 | 43.8 | 2.41 | 5.68 |

| JAGUAR 8600 (iii) HYDRATION TINE (MIN.) | 10% Pnt | NMD | % v < 100 μm | % V < 150 μm |
|---|---|---|---|---|
| 5 | 201.8 | 41.9 | 2.41 | 5.52 |
| 30 | 198.9 | 41.2 | 2.49 | 5.73 |
| 60 | 190.0 | 41.8 | 2.70 | 6.27 |

(i) NALCOTROL II is the trade name of Nalco Chemical Co. for its high molecular weight nonionic polyacrylamide.
(ii) JAGUAR 8000 is the trade name of Rhone-Poulenc Inc. for its 0.4 ms hydroxy propyl guar.
(iii) JAGUAR 8600 is the trade name of Rhone-Poulenc Inc. for its carboxymethyl hydroxy propyl guar.
(iv)Water typically has 6–7% by volume of droplets with diameter less than 100 mm when measured similarly.

The above results show that derivatized guars in water at 0.1% concentration are extremely effective at reducing the number of particles below 150 mm diameter and the spray volumes associated therewith. The initial effects are comparable to a polyacrylamide agricultural industry standard, however, the effectiveness of the derivatized guars does not deteriorate with time as is quite noticeable with the polyacrylamide. Although the polyacrylamide at five minutes had reduced the volume of liquid with drop size diameters below 150 mm to 4.72%, fifty-five (55) minutes later its effectiveness had deteriorated significantly, i.e., to the point where the volume below 150 mm had risen to 7.03%.

EXAMPLE II

The following are results realized during a study to examine the effect of high shear, such as that experienced in the field, upon the drift control agents of this invention using a polyacrylamide and water as the two controls.

The polymers were added to the spray tank as was done for the hydration/mixng studies of Example I. The mixtures were allowed to recycle freely (no pressure restriction) for two minutes prior to initial atomization (time zero) and then recycled with continuous pressure restriction to simulate field tank recycling while spraying was underway.

Droplet size spectra data were obtained along a single (90 second) traverse of the long axis of the spray cloud. The nozzle was then returned to the starting point (60 seconds); lines cleared of any formulation (15 seconds); and a new traverse started. This gives more or less a three minute interval between measurements, and essentially continuous shear stress. The process was repeated until the entire thirty (30) liters had been atomized, or less than 1 liter remained in the spray tank. Measurements recorded at approximately 3, 12, 24 and 35 minutes are shown below. The piston pump used for the experiments has a throughput of approximately 6.7 L/min. with no pressure restriction; 4.6 L/min. when spraying at 40 psi and 6 L/min. when restricted but not spraying.

TABLE II

| NALCOTROL II RECYCLING TIME (MIN.) | 10% Pnt | 90% Pnt | $D_{v0.5}$ | NMD | % V < 100 | % V < 150 |
|---|---|---|---|---|---|---|
| WATER (CONTROL) | 119.8 | 418.3 | 250.3 | 54.7 | 6.69 | 16.64 |
| 2.97 | 204.6 | 746.4 | 428.0 | 50.5 | 1.96 | 4.76 |
| 11.77 | 169.2 | 617.9 | 368.2 | 48.3 | 3.14 | 7.70 |
| 23.57 | 135.8 | 519.4 | 293.5 | 53.8 | 4.84 | 12.71 |
| 35.26 | 127.2 | 454.5 | 278.8 | 58.8 | 5.54 | 14.62 |

| JAGUAR 8000 RECYCLING TIME (MIN.) | 10% Pnt | 90% Pnt | $D_{v0.5}$ | NMD | % V < 100 | % V < 150 |
|---|---|---|---|---|---|---|
| 2.90 | 176.8 | 713.4 | 381.4 | 38.8 | 3.19 | 7.22 |
| 11.60 | 199.0 | 719.8 | 400.8 | 40.9 | 2.25 | 5.47 |
| 23.38 | 192.7 | 689.9 | 386.3 | 40.3 | 2.51 | 6.09 |
| 35.35 | 189.5 | 800.6 | 409.9 | 39.3 | 2.61 | 5.98 |

| JAGUAR 8600 RECYCLING TIME (MIN.) | 10% Pnt | 90% Pnt | $D_{v0.5}$ | NMD | % V < 100 | % V < 150 |
|---|---|---|---|---|---|---|
| 2.83 | 212.8 | 787.1 | 424.0 | 39.7 | 2.05 | 4.71 |
| 11.38 | 209.9 | 752.4 | 417.2 | 38.6 | 2.17 | 4.99 |
| 23.07 | 209.7 | 792.4 | 425.3 | 38.8 | 2.23 | 5.05 |
| 34.72 | 177.1 | 698.4 | 375.6 | 39.3 | 2.83 | 6.93 |

As can be seen from the above data, the polyacrylamide drift control agent shears quite significantly over time. The Volume Median Diameter ($D_{v0.5}$), i.e., the drop size below which 50% of the volume is contained in drops smaller, is initially fairly high for the polyacrylamide (428 mm), but drops off rapidly to below 280 mm, whereas the hydroxy propyl guar begins high and actually increases slightly with time from about 381 to about 410 mm. The carboxymethyl hydroxy propyl guar started high and stayed fairly constant at 424 mm (with a slight decrease to 376 at 35 minutes). Most importantly, the data shows that, as opposed to the polyacrylamide drift control agent, after approximately 35 minutes of recycling, the percent by volume of the spray composition contained in droplet sizes prone to drift, i.e., the <100 mm and <150 mm sizes, of the derivatized guars is not significantly different from what it was at three minutes. The polyacrylamide suffered a significant reduction in effectiveness during the same period of time.

EXAMPLE III

The following are results achieved during comparative high shear studies of a hydroxy propyl guar with other guars, i.e., a 1.2 ms hydroxy propyl guar, guar and a hydroxy propyl trimonium chloride guar.

The test conditions and procedures were identical to that used in the high shear recycle studies of Example II.

The wind tunnel is 4 meters wide, 4 meters high and 12 meters long, with an effective reach of 8 meters, housing a Mardrive track sprayer capable of handling a 5 nozzle boom (50 cm nozzle spacing) at boom speeds up to 20 km per hour. A 3 meters diameter, horizontally mounted, axial fan pulls air through the wind tunnel at velocities up to 8 meters per second. Airflow is approximately laminar for the center 3 meters width. Temperature and relative humidity are not controllable. The floor of the tunnel was covered with trays of stubble to act as an artificial crop.

To create the stubble, winter wheat was sown in 60×40 cm trays and grown outside. Shortly before heading, the wheat was sprayed off with paraquat and cut to a height of

TABLE III

| JAGUAR 8000 TIME (MIN.) | 10% Pnt | 90% Pnt | VMD | NMD | % V < 100 | % V < 150 |
|---|---|---|---|---|---|---|
| Water Control | 119.4 | 392.8 | 250.1 | 40.3 | 6.90 | 16.10 |
| 3.67 | 237.1 | 785.9 | 475.4 | 38.5 | 1.59 | 3.53 |
| 13.85 | 230.0 | 812.0 | 430.6 | 40.0 | 1.60 | 3.65 |
| 24.08 | 230.0 | 778.4 | 430.3 | 38.6 | 1.65 | 3.71 |
| 37.73 | 224.6 | 813.2 | 432.6 | 36.8 | 1.85 | 4.28 |

| JAGUAR 8012 (i) TIME (MIN.) | 10% Pnt | 90% Pnt | VMD | NMD | % V < 100 | % V < 150 |
|---|---|---|---|---|---|---|
| Water Control | 125.5 | 388.5 | 260.5 | 42.7 | 6.17 | 14.29 |
| 5.03 | 183.6 | 608.2 | 370.1 | 45.7 | 2.59 | 6.36 |
| 15.43 | 187.8 | 638.7 | 373.9 | 43.7 | 2.53 | 6.10 |
| 25.75 | 186.1 | 706.3 | 369.6 | 48.2 | 2.48 | 6.16 |
| 39.42 | 177.3 | 602.3 | 361.8 | 42.7 | 2.84 | 6.83 |

| JAGUAR 2610 (ii) TIME (MIN.) | 10% Pnt | 90% Pnt | VMD | NMD | % V < 100 | % V < 150 |
|---|---|---|---|---|---|---|
| Water Control | 126.3 | 392.4 | 256.6 | 40.7 | 6.18 | 14.46 |
| 3.43 | 194.6 | 700.4 | 383.6 | 36.5 | 2.56 | 5.58 |
| 13.82 | 192.2 | 625.5 | 381.4 | 37.7 | 2.63 | 5.96 |
| 24.13 | 191.7 | 656.3 | 380.4 | 37.0 | 2.62 | 5.91 |
| 38.00 | 181.4 | 687.1 | 374.2 | 35.9 | 3.02 | 6.65 |

| JAGUAR C-13S (iii) TIME (MIN.) | 10% Pnt | 90% Pnt | VMD | NMD | % V < 100 | % V < 150 |
|---|---|---|---|---|---|---|
| Water Control | 123.2 | 401.4 | 259.5 | 42.3 | 6.38 | 14.99 |
| 3.52 | 187.5 | 624.0 | 371.0 | 35.7 | 2.75 | 6.28 |
| 13.83 | 182.4 | 604.5 | 362.4 | 36.0 | 3.00 | 6.59 |
| 24.17 | 183.8 | 667.3 | 369.6 | 36.0 | 2.92 | 6.52 |
| 38.02 | 187.8 | 670.2 | 373.0 | 38.1 | 2.89 | 6.37 |

(i) JAGUAR 8012 is the trade name for 1.2 ms substituted hydroxy propyl guar sold by Rhone-Poulenc Inc.
(ii) JAGUAR 2610 is the trade name for non-derivatized guar sold by Rhone-Poulenc Inc.
(iii) JAGUAR C-13S is the trade name for hydroxy propyl trimonium chloride guar sold by Rhone-Poulenc Inc.

The above data confirms the effectiveness and essentially constant control of the drift droplets, i.e., those below 150 mmn realized by guar and derivatized guars during extended high shear recycling conditions.

EXAMPLE IV

A study was conducted in a wind tunnel at the Long Ashton Research Station in Bristol, England to evaluate the effect of pump shear on the downwind movement, i.e. the drift of a spray mixture containing 0.1% w/v JAGUAR 8000 in water and a spray mixture containing 0.0625% v/v Nalcotrol II in water, both compared with water above.

approximately 28 cm above soil level. For the edges of the wind tunnel, lower grade stubble was used (24 cm high) as guard rows.

The polymers were added to tap water and were applied through a static TeeJet XR8003VS nozzle at 40 psi mounted 45 cm above "crop" height. Half of each mixture was sprayed using a pressure can, i.e., no shear, and the other half was subjected to 10 minutes of recycling through a small piston pump before spraying. A fluorescent tracer (Fluorescein) was added to the spray solutions at 0.05% w/v.

The drift was measured at a single position 5 meters downwind from the boom and nozzles at five heights, (0:

crop height, 10, 28, 45, and 55 cm above crop height). Two wind velocities were used: nominally 2 and 4 meters per second. All applications were replicated three times.

Deposits on the drift collectors (string as supplied by WRK Inc. Manhattan Ks (66502) were extracted in 0.05M NaOH containing 0.05% Triton X100. Fluorescence was determined, within 1 hour of collection, using a Perkin-Elmer fluorescence spectrophotometer LS-2B (flow cell and peristaltic pump). Quantities of fluorescent material were determined from standard calibration curves derived from fresh standards.

The amount of drift for each treatment and at each height is expressed in terms of mg/g of tracer applied. Hence, the data can be related to "active ingredient" applied, irrespective of the volume applied. A summary of the data is presented in Table IV below.

TABLE IV

| Centimeters Above Crop Height | 55 | 45 | 28 | 10 | 0 |
|---|---|---|---|---|---|
| Tracer Drift (µg/g of tracer applied) Nominal Wind Speed 2 Meters/Second | | | | | |
| Water | 0.296 | 0.779 | 2.350 | 3.874 | 4.211 |
| Nalcotrol II Pressure Can | 0.091 | 0.220 | 0.678 | 1.103 | 1.152 |
| Nalcotrol II Sheared | 0.160 | 0.396 | 1.250 | 2.073 | 2.289 |
| JAGUAR 8000 Pressure Can | 0.091 | 0.206 | 0.770 | 1.365 | 1.555 |
| JAGUAR Sheared | 0.080 | 0.206 | 0.749 | 1.372 | 1.522 |
| Nominal Wind Speed 4 Meters/Second | | | | | |
| Water | 0.370 | 2.029 | 16.899 | 44.227 | 54.440 |
| Nalcotrol II Pressure Can | 0.157 | 0.882 | 8.181 | 18.685 | 21.404 |
| Nalcotrol II Sheared | 0.147 | 0.818 | 13.471 | 37.125 | 47.656 |
| JAGUAR 8000 Pressure Can | 0.109 | 0.494 | 7.181 | 19.975 | 22.410 |
| JAGUAR Sheared | 0.076 | 0.493 | 7.286 | 21.025 | 23.576 |

At "crop height" and nominal wind speed of 2 meters/second, JAGUAR 8000, both sheared and unsheared, reduced drift by about 64%, whereas sheared Nalcotrol II reduced drift by only about 45%.

At nominal wind speed of 4 meters/second, there was essentially no difference between the mixtures containing the sheared and unsheared JAGUAR 8000 and the unsheared Nalcotrol II; a reduction effect of about 60%. However, the sheared Nalcotrol II polyacrylamide drifted nearly as much as water alone.

Thus, this simulated field study data show that a derivatized guar, both sheared and unsheared, can reduce drift as effectively as an unsheared polyacrylamide drift control standard. Furthermore, both sheared and unsheared derivatized guar can reduce drift significantly compared to a sheared polyacrylamide drift control standard.

EXAMPLE V

Aqueous compositions containing sixteen (16) additional commercial drift reduction products were tested under the procedures set forth in Example II. As JAGUAR 8000 and Nalcotrol II yielded viscosities of 2.4 cP at our test concentrations, the required concentration of each test material was identified to yield approximately the same viscosity. The products included both cold and hot water soluble polymers.

All viscosity measurements in the Examples were made using the Contraves Low Shear 40 Viscometer (LS40). Temperature was controlled at 25.0° C. using a circulating water bath. The LS40 uses Couette geometry (cup and bob) and the fixture designated DIN 412 was used for the measurements. The materials selected and their respective concentrations and viscosities are set forth in Table Va.

TABLE Va

| Trade Name | Description | Supplier | Conc. | Test Viscosity (cP) |
|---|---|---|---|---|
| JAGUAR 8000 | HP guar | RPI | 0.10 | 2.4 |
| Nalcotrol II | polyacrylamide | Nalco | 0.0625 | 2.4 |
| SeaSpen PF | carrageenan | FMC | 0.05 | 2.4 |
| Viscarin GP 209 | carrageenan | FMC | 0.05 | 5.1 |
| Viscarin SD 389 | carrageenan | FMC | 0.075 | 3.2 |
| Klucel M | HP cellulose | Aqualon | 0.10 | 2.2 |
| Cellulose Gum L | Na CM cellulose | Aqalon | 0.10 | 3.4 |
| Cellulose Gum 250MR | HE cellulose | Aqualon | 0.17 | 2.5 |
| Pemulen TR-1 | Acrylic copolymer | Goodrich | 0.125 | 2.1 |
| Gum Arabic, Tech. | — | AEP Colloids | 3.10 | 2.3 |
| Locust Bean Gum | — | Meer | 0.20 | 2.3 |
| Tragacanth Gum | — | Meer | 0.10 | 1.9 |
| Polyox 301 | poly(ethylene oxide) | U. Carbide | 0.12 | 2.4 |
| Polyox Coagulant | poly(ethylene oxide) | U. Carbide | 0.07 | 2.5 |
| K9A50 | gellan gum | Kelco | 0.07 | 2.1 |
| K1A96 | whelan gum | Kelco | 0.025 | 2.6 |
| K1A112 | rhamsan gum | Kelco | 0.012 | 2.2 |
| Luviskol K90 | poly(vinyl pyrrolidone) | BASF | 0.70 | 2.7 |

Table Vb reflects the drift-prone particle size distributions and the change in this distribution as a function of recycle shear time.

B. The viscosity at 100 reciprocal seconds ($sec^{-1}$) of shear was measured.

TABLE Vb

| PRODUCT | % Volume at Start 100 μm | % Volume at Start <150 μm | % Volume at End <100 μm | % Volume at End <150 μm | % Change * <100 μm | % Change * <150 μm |
|---|---|---|---|---|---|---|
| Water | 5.8 | 13.9 | 5.5 | 12.8 | −5.2 | −8.5 |
| JAGUAR 8000 - HP guar | 1.8 | 3.8 | 2.2 | 4.8 | −22.2 | −26.3 |
| Nalcotrol II - polyacrylamide | 2.0 | 4.7 | 3.8 | 10.8 | −90.0 | −129.8 |
| SeaSpen PF - carrageenan | 4.3 | 9.9 | 4.4 | 10.7 | −2.5 | −8.1 |
| Viscarin GP 209 - carrageenan | 3.8 | 8.9 | 3.7 | 8.9 | +2.6 | 0 |
| Viscarin SD 389 - carrageenan | 3.7 | 8.3 | 4.7 | 11.1 | −27.0 | −34.6 |
| Klucel M - HP Cellulose | 3.3 | 8.1 | 3.5 | 8.5 | −6.1 | −4.9 |
| Cellulose Gum 7M - Na CMC | 4.7 | 10.6 | 4.6 | 11.0 | +2.1 | −3.8 |
| Cellulose Gum 250MR - HEC | 2.9 | 6.4 | 3.4 | 8.0 | −17.2 | 25.0 |
| Pemulen TR-1 - Acrylic copol. | 4.4 | 10.8 | 4.9 | 12.2 | −11.4 | −13.0 |
| Gum Arabic, Tech. | 5.1 | 12.4 | 5.7 | 13.4 | −11.8 | −8.1 |
| Locust Bean Gum | 4.0 | 9.8 | 4.1 | 9.9 | −2.5 | −1.0 |
| Tragacanth Gum | 4.6 | 10.2 | 4.1 | 9.7 | +21.7 | +4.9 |
| Polyox 301 - PEO | 0.1 | 0.2 | 2.1 | 4.7 | −2000 | −2250 |
| Polyox Coagulant - PEO | 0.1 | 0.3 | 3.8 | 9.0 | −3700 | −2900 |
| K9A50 - gellan gum | 4.1 | 10.0 | 4.4 | 10.4 | −7.3 | −4.0 |
| K1A96 - whelan gum | 3.5 | 8.6 | 4.7 | 11.3 | −30.6 | −31.4 |
| K1A112 - rhamsan gum | 2.2 | 6.7 | 4.1 | 9.9 | −86.4 | −34.0 |
| Luviskol K90 - PVP | 4.1 | 9.4 | 4.5 | 10.0 | −9.8 | −6.4 |

* (+) change is favorable; volume decreased with time.
(−) is unfavorable; volume increased with time.
Based on water behavior; +/−8.5% (or greater) may not be significant.

None of the compounds tested provided as much drift protection as JAGUAR 8000 when judged by the percent of spray volume in droplets less than 100 or 500 microns. Only Polyox 301 and Polyox Coagulant (both polyethylene oxides) provided more initial drift protection, but these compounds atomized poorly and sheared extremely rapidly. As an aside, the "301" and "Coagulant" products did not atomize well until sheared and so initial droplet counts for them were below 1,000.

JAGUAR 8000 resisted shear degradations very well, essentially maintaining its droplet size spectrum over the approximately 40 minutes of the test.

EXAMPLE VI

Tests were run to establish the upper concentration that could be utilized with guar and its derivatives to ensure the Newtonian properties necessary to keep the drift reduction effects constant under the shearing conditions likely to be encountered in commercial spray applications. By Newtonian behavior, we mean that there be less than a 20% loss in viscosity at 100 $sec.^{-1}$ shear relative to the average viscosity between 0.1 and 1.0 $sec.^{-1}$ shear. If greater than a 20% loss occurs, the composition will be assumed to be non-Newtonian, i.e., visco-elastic.

The viscosity profiles of a non-derivatized guar and two derivatized guars were examined.

The adjuvant was added to test water (tap water or otherwise specified hardness) at room temperature (20°–25° C.). With high-speed mixing, the drift reduction adjuvant was thoroughly mixed and hydrated. This is nominally accomplished within 45 seconds.

The solution was de-aerated (to remove foam or entrained air) by pulling a vacuum over its surface or by centrifugation.

The viscosity was measured.

A. The average viscosity between 0.1 and 1.0 reciprocal seconds ($sec^{-1}$) of shear was determined.

The following table summarizes the results of the viscosity tests.

TABLE VI

Rheological Data Summary

| Guar/Guar Derivative | Ave. Visc. (cP) (0.1–1.0 $sec^{-1}$) | Visc. (cP) @ 100 $sec^{-1}$ | % |
|---|---|---|---|
| JAGUAR 8000 | | | |
| 0.25% | 35.39 | 19.25 | −45.6 |
| 0.20% | 18.49 | 12.38 | −33.0 |
| 0.15% | 9.03 | 7.39 | −18.2 |
| 0.125% | 8.01 | 6.48 | −19.2 |
| 0.100% | 4.89 | 4.40 | −10.0 |
| 0.075% | 3.36 | 3.11 | −7.7 |
| JAGUAR 8012 | | | |
| 0.25% | 11.14 | 9.50 | −14.8 |
| 0.20% | 6.98 | 6.56 | −6.1 |
| 0.15% | 4.21 | 4.31 | +2.3 |
| JAGUAR 2610 | | | |
| 0.20% | 12.81 | 10.26 | −19.9 |
| 0.15% | 6.63 | 6.15 | −7.2 |
| 0.10% | 3.10 | 3.37 | +8.8 |
| JAGUAR C-13S | | | |
| 0.15% | 24.23 | 14.09 | −41.9 |
| 0.10% | 9.90 | 7.48 | −24.5 |
| 0.05% | 3.17 | 3.19 | +0.5 |

In view of the above, the upper concentration of guar and its derivatives in aqueous compositions has been determined to be that which establishes a viscosity of about 7.5 cP or less at 100 $sec^{-1}$. Depending on the nature of the guar or its derivative, the concentration range required to achieve this viscosity will vary. For guar, the concentration range is 0.075 to less than 0.2% weight per unit volume, preferably from 0.075 to 0.18% w/v. For non-cationic derivatized guars such as hydroxy propyl guar or carboxy methyl hydroxy propyl guar, the concentration range is 0.075 to 0.275% w/v, preferably 0.1 to 0.125% w/v. For cationic guars such as hydroxy propyl trimethyl ammonium chloride guar, the concentration range is from 0.05 to 0.1% w/v. For blends of the above, the concentration range is from 0.05 to 0.275% w/v with the proviso that i) the cationic guar concentration not exceed 0.1% w/v; and ii) the non-derivatized guar concentration be less than 0.2% w/v.

EXAMPLE VII

A study of the reflection/retention of Nalcotrol II (N2, Nalco Chemical Co., Naperville, Ill.) representing the industry standard, polyacrylamide polymers; and AgRHÔ DR-2000® (DR, Rhône-Poulenc Inc., Surfactants and Specialties, Cranbury, N.J.), a derivatized guar of the present invention (hydroxy propyl derivatized guar). A spray mixture of N2 at 0.62 ml/l and water was prepared. A spray mixture of D2 at 1 g/l and water was prepared. The levels of N2 and DR are the standard recommended levels of use. Tap water was utilized. A fluorescent tracer (Rhodamine WT at 0.8% v/v) was utilized in each of the spray mixtures. A control of tap water with tracer was also used. The droplet reflection/retention from glasshouse grown cabbage (*Brassica oleracea*) leaves was determined using a standard reflection chamber as shown in FIG. 1. See Crease, G. J., Hall, F. R., and Thacker, J. R. M. 1991: *J Environ. Sci. Health* B26: 383–407 which is incorporated herein by reference.

The spray mixtures were applied through XR 8003 tips (Spraying Systems, Wheaton Ill.) at 275 kPa with a 45 cm boom height. Sprayer speed was 7.7 km/h, resulting in an applied volume of 180 l/ha. Impinging drops were either retained by the angled leaf or reflected from the leaf onto a glass plate positioned adjacent to the leaf. After spraying the glass or leaf surfaces were washed in 95% ethanol to collect the deposits. The leaves were inverted into a beaker containing approximately 80 ml 95% ethanol. They were washed by gentle agitation in the ethanol for approximately one minute, then the dye/ethanol solution was transferred to a volumetric flask, topped up to 100 ml, and finally transferred to a storage bottle which was capped and placed in the dark until analysis. Recovery efficiency of this washing technique was approximately 95%. The ethanol/dye solutions were analyzed for dye content on a Turner Fluorescence Spectrophotometer (Model 112), and readings were converted to parts per billion through standard curves and later to $\mu$g dye per plant. The deposits were then quantified using standard fluorimetric techniques. See Richardson, R. G. 1984: *Australian Weeds* 4: 123–124 which is incorporated herein by reference.

The glasshouse grown cabbage leaves, used as a model "difficult to wet" surface, reflected 60 to 80% of impinging spray droplets. Approximately 30% less spray was reflected from mixtures containing DR compared to either water alone or water containing N2. The spray droplet reflection from angled cabbage leaves as affected by spray adjuvant is graphically represented in FIG. 2.

It can therefore be concluded that guar and derivatives of guar can significantly aid deposition and retention.

EXAMPLE VIII

A study of the effect of the addition of either conventional polyacrylamide adjuvants or the adjuvants of the present invention to glyphosate was conducted. Glyphosate, N-(phosphonomethyl)glycine, is a common herbicide. Glyphosate supplied by Monsanto Company, St. Louis, Mo., as Roundup™ Super Concentrate was utilized. The Roundup™ was applied alone or in mixture with AgRHÔ DR-2000® or Nalcotrol II to velvetleaf (*Abutilon theophrastii*) at three rates (0.56, 1.12 and 1.68 kg ae/ha) through a three nozzle boom equipped with XR 8003 VS tips operating at 275 kPa and applying 180 L/ha spray solution. AgRHÔ DR-2000® and Nalcotrol II were utilized at the supplier recommended levels of 1 g/l and 0.62 ml/l respectively. Sprayed plants were visually assessed for herbicide phytotoxicity (on a 0–10 scale) at 3 day intervals. At 14 days after spraying, plants were clipped at soil level and shoot biomass was determined. Shoots were oven dried at 60°–80° C. for 24 to 48 hours, after which shoot dry weights were determined. Shoot biomass was recorded 14 days after treatment and nonlinear regression equations were fitted to the data to determine the $GR_{50}$ values. See Brian, P. and Cousens, R. 1989: *Weed Res.* 29:93–96 which is incorporated herein by reference. A single petri dish was placed in line with the plant to be sprayed so that the actual amount of spray presented to the target could be measured. Therefore, the total relative amounts of spray presented to the target could be determined from the petri dish data. This permitted normalization of the herbicide rates to account for differences in patternation by the various adjuvants. Differences in efficacy observed after this normalization could then be taken to be due to differences in deposit behavior and not the amount of spray present.

The efficacy of glyphosate was enhanced by the presence of AgRHÔ DR-2000® and therefore it can be concluded that guar and/or derivatives of guar can enhance/improve the bioefficacy of bioactives.

Figure 3:
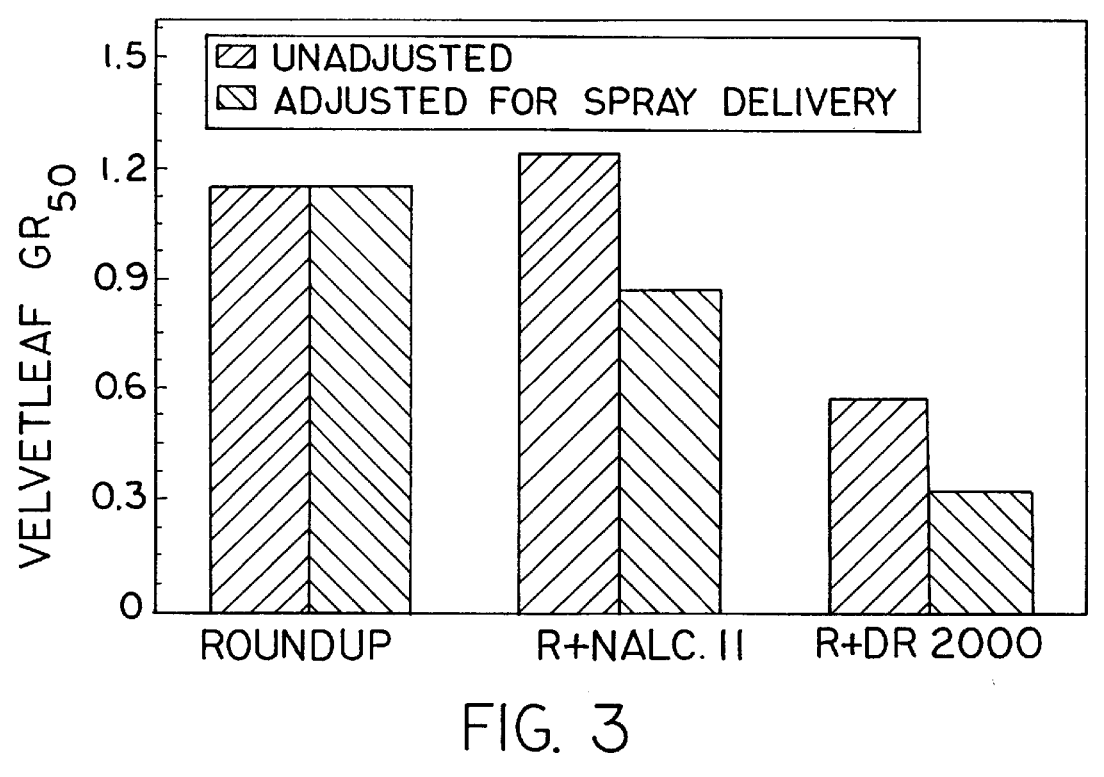

As graphically represented in FIG. 3, $GR_{50}$ values were significantly lower for glyphosate plus DR than for glyphosate alone, especially when herbicide rates were adjusted for the quantity of spray presented to the plants. These data suggest that guar and/or derivatives of guar have properties which counteract the negative effects of uneven spray distributions or the presentation of coarser sprays to the plant canopy. One of which is the character by which it maintains a droplet in the position of deposit without movement away from the initial point of contact and maintains a higher equilibrium moisture content than would occur without it being present. See Knoche, M. 1994: *Crop Prot* 13: 163–178 which is incorporated herein by reference. Glyphosate deposits were more efficacious in the presence of the biodegradable polymer, reducing $GR_{50}$ values significantly. It is hypothesized that the surface properties of the additives of the present invention play a role in the uptake and translocation of xenobiotics in plant systems. It can be concluded that the adjuvants of the present invention significantly enhance bioefficacy of bioactives, such as herbicides.

While the embodiments of the invention chosen herein for purposes of disclosure are considered to be preferred, it is to be understood that this invention is intended to cover all changes and modifications in the disclosed embodiments which fall within the spirit and scope of the invention.

What is claimed is:

1. A method for improving the deposition characteristics of a dilute aqueous composition during the aerial spraying or discharge thereof, said improvement comprising mixing a deposition aid selected from the group consisting of non-derivatized guar, derivatives of guar, and mixtures thereof into said aqueous composition prior to its spraying or discharge in an amount sufficient that if mixed in water alone said deposition aid and the water would exhibit Newtonian behavior.

2. The method of claim 1 wherein said deposition aid is a non-derivatized guar that is mixed into the aqueous solution in an amount of from about 0.035% to about 0.20% weight per unit volume at final dilution.

3. The method of claim 2 wherein the deposition aid is from 0.075% to 0.18% weight per unit volume.

4. The method of claim 2 wherein said aqueous composition contains a bioactively effective amount of a bioactive.

5. The method of claim 4 wherein said bioactive is a pesticide.

6. The method of claim 1 whereby the deposition aid functions as the sole deposition aid and as a bioefficacy aid.

7. A method for improving the deposition characteristics of a dilute aqueous composition during aerial spraying or discharge thereof, said improvement comprising the mixing into said aqueous composition of a deposition aid consisting essentially of non-cationic derivatized guar in an amount of from about 0.035% to about 0.275% weight per unit volume at final dilution.

8. The method of claim 7 wherein the deposition aid is from 0.04% to 0.11% weight per unit volume.

9. The method of claim 7 wherein said non-cationic derivatized guar is a hydroxy propyl derivatized guar.

10. The method of claim 9 wherein the deposition aid is from 0.04% to 0.11% weight per unit volume.

11. The method of claim 9 wherein said hydroxy propyl derivatized guar is a carboxymethyl hydroxy propyl derivatized guar.

12. The method of claim 11 wherein the deposition aid is from 0.04% to 0.11% weight per unit volume.

13. The method of claim 11 wherein said aqueous composition contains a bioactively effective amount of a bioactive.

14. The method of claim 13 wherein said bioactive is a pesticide.

15. The method of claim 9 wherein said aqueous composition contains a bioactively effective amount of a bioactive.

16. The method of claim 15 wherein said bioactive is a pesticide.

17. The method of claim 7 wherein said aqueous composition contains a bioactively effective amount of a bioactive.

18. The method of claim 17 wherein said bioactive is a pesticide.

19. A method for improving the deposition characteristic of a dilute aqueous composition during the aerial spraying or discharge thereof, said improvement comprising the mixing into said aqueous composition of a deposition aid consisting essentially of cationic derivatized guar in an amount of from about 0.025% to about 0.1% weight per unit volume at final dilution.

20. The method of claim 19 further comprising the addition of a non-derivatized guar such that the concentration of said non-derivatized guar does not exceed 0.2% weight per unit volume and said cationic derivatized guar does not exceed 0.1% weight per unit volume.

21. The method of claim 20 wherein said aqueous composition contains a bioactively effective amount of a bioactive selected from the group consisting of pesticides, growth regulators and combinations thereof.

22. The method of claim 19 wherein said aqueous composition contains a bioactively effective amount of a bioactive.

23. A method for improving the bioefficacy of bioactive compounds in a dilute aqueous composition during the aerial spraying or discharge thereof, said improvement comprising mixing a bioefficacy aid selected from the group consisting of non-derivatized guar, non-cationic derivatized guar, cationic derivatexed guar and mixtures thereof into said aqueous composition prior to its spraying or discharge in an amount sufficient that if mixed in water alone said bioefficacy aid and the water exhibit Newtonian behavior.

24. The method of claim 23 wherein said bioefficacy aid consists essentially of non-derivatized guar which is mixed into the dilute aqueous composition in an amount of from about 0.035% to about 0.20% weight per unit volume at final dilution.

25. The method of claim 24 wherein the bioefficacy aid is from 0.075% to 0.18% weight per unit volume.

26. The method of claim 23 whereby the bioefficacy aid also functions as the sole deposition aid.

27. The method of claim 23 wherein said bioefficacy aid consists essentially of a non-cationic derivatized guar which is mixed into the dilute aqueous composition in an amount of from about 0.035% to about 0.275% weight per unit volume at final dilution.

28. The method of claim 27 wherein the bioefficacy aid is from 0.04% to 0.11% weight per unit volume.

29. The method of claim 23 wherein said non-cationic derivatized guar consists essentially of hydroxypropyl derivatized guar that is mixed into the dilute aqueous solution in an amount of from about 0.035% to about 0.275% weight per unit volume at final dilution.

30. The method of claim 29 wherein the bioefficacy aid is from 0.04% to 0.11% weight per unit volume.

31. The method of claim 23 wherein said non-cationic derivatized guar consists essentially of carboxymethyl hydroxypropyl derivatized guar that is mixed in the dilute aqueous solution in an amount of from about 0.035% to about 0.275% weight per unit volume at final dilution.

32. The method of claim 31 wherein the bioefficacy aid is from 0.04% to 0.11% weight per unit volume.

33. A method for improving the bioefficacy of bioactives in a dilute aqueous composition during the aerial spraying or discharge thereof, said improvement comprising mixing a bioefficacy aid consisting essentially of cationic derivatized guar into said aqueous composition in an amount of from about 0.025% to 0.1% weight per unit volume at final solution.

34. A method for improving the bioefficacy of an aqueous composition comprising one or more bioactive compounds and water during the aerial spraying or discharge thereof, said improvement comprising the addition of a bioefficacy aid selected from the group consisting of non-derivatized guar, non-cationic derivatized guar, cationic derivatized guar and combinations thereof to said aqueous composition prior to its aerial spraying or discharge in an amount such that the cationic derivatized guar concentration does not exceed 0.1% weight per unit volume and the non-derivatized guar concentration does not exceed 0.2% weight per unit volume.

35. A deposition enhanced spray composition comprising at final dilution:

a) a major amount of water; and b) from 0.025% to 0.275% weight per unit volume of non-derivatized guar, non-cationic derivatized guar, cationic derivatized guar or combinations thereof; wherein i) the cationic derivatized guar concentration does not exceed 0.1% weight per unit volume; and ii) the non-derivatized guar concentration does not exceed 0.2% weight per unit volume; and whereby said non-derivatized guar, non-cationic derivatized guar, cationic derivatized guar or combinations thereof function as the sole deposition aid, and as a bioefficacy aid.

* * * * *